(12) United States Patent
Miyamoto (10) Patent No.: US 10,896,501 B2
(45) Date of Patent: Jan. 19, 2021

(54) RIB DEVELOPED IMAGE GENERATION APPARATUS USING A CORE LINE, METHOD, AND PROGRAM

(71) Applicant: FUJIFILM Corporation, Tokyo (JP)

(72) Inventor: Masaki Miyamoto, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 78 days.

(21) Appl. No.: 16/240,099

(22) Filed: Jan. 4, 2019

(65) Prior Publication Data

US 2019/0236776 A1  Aug. 1, 2019

(30) Foreign Application Priority Data

Jan. 30, 2018  (JP) .................................. 2018-013433

(51) Int. Cl.
*G06T 7/00* (2017.01)
*A61B 6/00* (2006.01)
*G06T 15/08* (2011.01)

(52) U.S. Cl.
CPC ............ *G06T 7/0012* (2013.01); *A61B 6/466* (2013.01); *G06T 15/08* (2013.01); *A61B 2576/00* (2013.01); *G06T 2207/10081* (2013.01); *G06T 2207/30008* (2013.01); *G06T 2210/41* (2013.01); *G06T 2215/06* (2013.01)

(58) Field of Classification Search
None
See application file for complete search history.

(56) References Cited

U.S. PATENT DOCUMENTS

| | | | |
|---|---|---|---|
| 7,804,986 B2 * | 9/2010 | Lai ......................... | A61B 5/055 382/128 |
| 9,189,847 B2 | 11/2015 | Gnanamani et al. | |
| 2003/0171814 A1 * | 9/2003 | Muhanna ................ | A61F 2/442 623/17.11 |
| 2007/0223799 A1 * | 9/2007 | Weiss ........................ | G06T 7/11 382/131 |
| 2012/0008960 A1 * | 1/2012 | Kubo ..................... | G08C 23/04 398/106 |
| 2012/0197298 A1 * | 8/2012 | Baccelli ............... | A61B 17/707 606/264 |

OTHER PUBLICATIONS

Ramakrishnan et al., "Automatic Three-Dimensional Rib Centerline Extraction from CT Scans For Enhanced Visualization and Anatomical Context", Proc. of SPIE, Mar. 14, 2011, Medical Imaging 2011: Image Processing, vol. 7962, 79622X, 13 pages.

* cited by examiner

*Primary Examiner* — Tahmina N Ansari
(74) *Attorney, Agent, or Firm* — Birch, Stewart, Kolasch & Birch, LLP (57) ABSTRACT

A rib extraction unit extracts a rib from a three-dimensional image, a core line setting unit sets a core line of the rib, and a specific axis direction determination unit determines a specific axis direction in a cross section crossing the core line of the rib. An image generation unit moves a position of the core line in the specific axis direction according to an instruction to move the core line in the specific axis direction and generates a developed image of at least one rib based on a cross section along the core line at the moved position.

8 Claims, 7 Drawing Sheets

RIB DEVELOPED IMAGE GENERATION APPARATUS USING A CORE LINE, METHOD, AND PROGRAM

CROSS REFERENCE TO RELATED APPLICATIONS

The present application claims priority under 35 U.S.C. § 119 to Japanese Patent Application No. 2018-013433 filed on Jan. 30, 2018. The above application is hereby expressly incorporated by reference, in its entirety, into the present application.

BACKGROUND

Technical Filed

The present invention relates to a rib developed image generation apparatus, method, and program for generating a developed image showing a cross section along the longitudinal direction of the ribs.

Related Art

In recent years, advances in medical apparatuses, such as computed tomography (CT) apparatuses and magnetic resonance imaging (MRI) apparatuses, have enabled image diagnosis using high-resolution medical images with higher quality. Three-dimensional images acquired by the CT apparatus and the MRI apparatus are configured to include a large number of two-dimensional images and have a large amount of information. For this reason, it may take time for a doctor to find and examine a desired observation part. Therefore, it has been practiced to improve the efficiency of diagnosis by enhancing the visibility of the entire organ or a lesion by recognizing an organ of interest and performing maximum intensity projection (MIP) processing, minimum Intensity projection (MinIP) processing, multiplanar reconstruction (MPR) processing, curved planar reconstruction (CPR) processing, and the like on a three-dimensional image including the organ of interest. In particular, the CPR processing is to generate a CPR image by designating a certain curved surface in a three-dimensional image and reconstructing the three-dimensional image along the designated curved surface into a two-dimensional image. As a result, it is possible to display a cross section in the longitudinal direction on one screen regarding the form of the inner wall surface of a tubular structure or the form of the inside of the bone.

On the other hand, in order to examine the fracture of the ribs of a patient or the metastasis of a disease, such as cancer, to the ribs, a method of generating a CPR image of the ribs by performing CPR processing on the three-dimensional image of the ribs has been proposed (for example, refer to U.S. Pat. No. 9,189,847B). In addition, a method for appropriately extracting the center line of the ribs at the time of generating a CPR image of the ribs has also been proposed (refer to Sowmya Ramakrishnan, Christopher Alvino, Leo Grady, Atilla Kiraly, "Automatic three-dimensional rib centerline extraction from CT scans for enhanced visualization and anatomical context", Proc. SPIE 7962, Medical Imaging 2011: Image Processing, 79622X (14 Mar. 2011); doi: 10.1117/12.878283; http://dx.doi.org/10.1117/12.878283). In the CPR image, each rib is shown in a linearly developed state. For this reason, the CPR image of the ribs is referred to as a developed image. In the developed image of the ribs, since the ribs are linear, it is easy to observe a fractured portion or a portion where a tumor has spread. Therefore, it is possible to accurately examine the ribs by using the developed image of the ribs. In particular, in the method disclosed in U.S. Pat. No. 9,189,847B, it is possible to observe the ribs in a plurality of cross sections with the central axis as a reference by rotating the cross section in which the ribs are developed around the central axis of the ribs. As a result, since it is possible to observe the inside of the ribs to every corner, it is possible to examine the ribs more accurately.

However, in a case where the cross section in which the ribs are developed is rotated around the central axis of the ribs as in the method disclosed in U.S. Pat. No. 9,189,847B, the vertical direction of the developed image does not match the vertical direction of the human body (that is, the body axis direction of the human body). That is, the vertical direction of the developed image matches the body axis direction of the human body in a state in which the developed image is displayed first, but the vertical direction of the developed image does not match the body axis direction of the human body in a case where the cross section in which the ribs are developed is rotated around the central axis of the ribs. For this reason, in the method disclosed in U.S. Pat. No. 9,189,847B, it is not known which direction matches the body axis direction of the human body in the displayed developed image.

SUMMARY

The invention has been made in view of the above circumstances, and it is an object of the invention to make it possible to easily recognize a direction of a cross section, in which a developed image of the ribs is generated, with respect to a human body in the developed image.

A rib developed image generation apparatus according to the invention comprises: a rib extraction unit that extracts at least one rib from a three-dimensional image including ribs; a core line setting unit that sets a core line of the at least one rib; a specific axis direction determination unit that determines a specific axis direction in a cross section crossing the core line of the at least one rib; and an image generation unit that moves a position of the core line in the specific axis direction according to an instruction to move the core line in the specific axis direction and generates a developed image of the at least one rib based on a cross section along the core line at the moved position.

"Core line" means the center line of the ribs connecting the centers (centers of gravity) of the cross sections of the ribs. In the invention, the core line is moved in a specific axis direction crossing the cross section of the ribs. As a result of the movement, the core line does not pass through the center (center of gravity) of each cross section of the ribs. In the present embodiment, however, a line moved in the specific axis direction is also referred to as a core line.

The rib developed image generation apparatus according to the invention may further comprise a display control unit that displays the developed image on a display unit.

In the rib developed image generation apparatus according to the invention, the display control unit may display a combined image, which is obtained by combining the developed images of a plurality of ribs, on the display unit.

In the rib developed image generation apparatus according to the invention, the display control unit may display the combined image on the display unit such that the plurality of ribs are associated with vertebrae.

In the rib developed image generation apparatus according to the invention, the image generation unit may move the core line at equal intervals in the specific axis direction for the plurality of ribs.

In the rib developed image generation apparatus according to the invention, the image generation unit may move the core line at a rate corresponding to a length in the specific axis direction for the plurality of ribs.

A rib developed image generation method according to the invention comprises: extracting at least one rib from a three-dimensional image including ribs; setting a core line of the at least one rib; determining a specific axis direction in a cross section crossing the core line of the at least one rib; and moving a position of the core line in the specific axis direction according to an instruction to move the core line in the specific axis direction and generating a developed image of the at least one rib based on a cross section along the core line at the moved position.

In addition, a program causing a computer to execute the rib developed image generation method according to the present invention may be provided.

Another rib developed image generation apparatus according to the invention comprises: a memory that stores commands to be executed by a computer; and a processor configured to execute the stored commands. The processor executes: processing for extracting at least one rib from a three-dimensional image including ribs; processing for setting a core line of the at least one rib; processing for determining a specific axis direction in a cross section crossing the core line of the at least one rib; and processing for moving a position of the core line according to an instruction to move the core line in the specific axis direction and generating a developed image of the at least one rib based on a cross section along the core line at the moved position.

According to the invention, at least one rib is extracted from the three-dimensional image including ribs, and the core line of the at least one rib is extracted. Then, a specific axis direction in the cross section crossing the core line of the at least one rib is determined, and the position of the core line is moved in the specific axis direction according to the movement instruction and the developed image of at least one rib is generated based on the cross section along the core line at the moved position. For this reason, even in a case where the core line is moved, the direction of the cross section defined by the generated developed image is not changed. Therefore, even in a case where the cross section where the developed image is generated in the rib is changed, the direction in the human body is not changed in the displayed developed image. As a result, in a case where the developed image of whichever cross section is displayed, it is possible to recognize which direction in the human body the cross section of the developed image faces.

DETAILED DESCRIPTION

Figure 1:
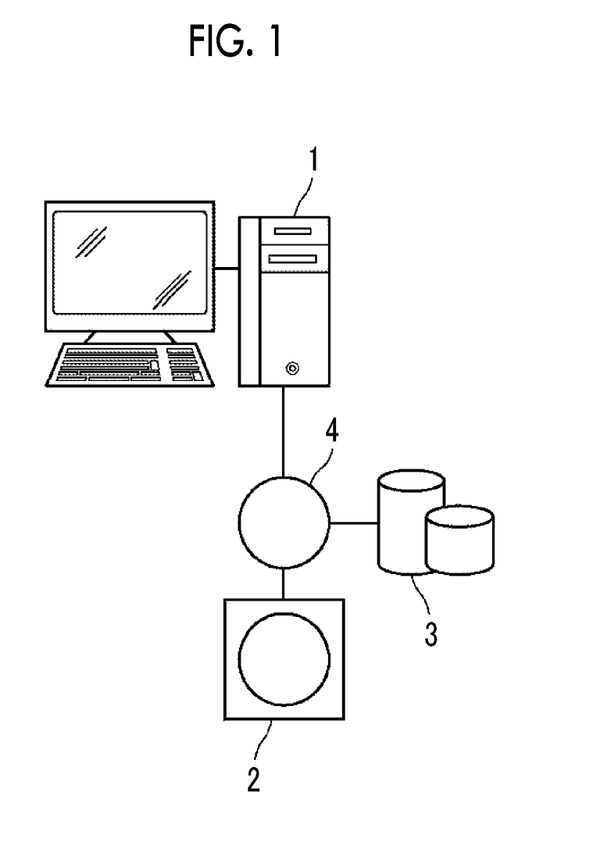
FIG. 1 is a hardware configuration diagram showing an outline of a diagnostic support system to which a rib developed image generation apparatus according to an embodiment of the invention is applied.

Hereinafter, an embodiment of the invention will be described with reference to the accompanying diagrams. FIG. 1 is a hardware configuration diagram showing the outline of a diagnostic support system to which a rib developed image generation apparatus according to a first embodiment of the invention is applied. As shown in FIG. 1, in the diagnostic support system, a rib developed image generation apparatus 1 according to the present embodiment, a three-dimensional image capturing apparatus 2, and an image storage server 3 are communicably connected to each other through a network 4. Then, in the diagnostic support system, a developed image that is a CPR image of the ribs as a diagnostic target of a subject is generated in the rib developed image generation apparatus 1.

The three-dimensional image capturing apparatus 2 is an apparatus that generates a three-dimensional image showing a diagnostic target part of a subject by imaging the diagnostic target part. Specifically, the three-dimensional image capturing apparatus 2 is a CT apparatus, an MRI apparatus, a positron emission tomography (PET) apparatus, or the like. The three-dimensional image generated by the three-dimensional image capturing apparatus 2 is transmitted to the image storage server 3 and stored therein. In the present embodiment, it is assumed that the diagnostic target part of the subject is the ribs, the three-dimensional image capturing apparatus 2 is a CT apparatus, and a three-dimensional image of the chest of the subject is generated.

The image storage server 3 is a computer that stores and manages various kinds of data, and comprises a large-capacity external storage device and software for database management. The image storage server 3 communicates with other devices through the wired or wireless network 4 to transmit and receive image data or the like. Specifically, the image storage server 3 acquires image data, such as a three-dimensional image generated by the three-dimensional image capturing apparatus 2, through the network, and stores the image data in a recording medium, such as a large-capacity external storage device, to manage the image data. The storage format of image data and the communication between devices through the network 4 are based on a protocol, such as a digital imaging and communication in medicine (DICOM).

The rib developed image generation apparatus 1 is realized by installing a rib developed image generation program according to an embodiment of the invention on one computer. The computer may be a workstation or a personal computer that is directly operated by a doctor who performs diagnosis, or may be a server computer connected to these through a network. The rib developed image generation program is distributed by being recorded on a recording medium, such as a digital versatile disc (DVD) or a compact disk read only memory (CD-ROM), and is installed onto the computer from the recording medium. Alternatively, the image display program is stored in a storage device of a server computer connected to the network or in a network storage so as to be accessible from the outside, and is downloaded and installed onto a computer used by a doctor as necessary.

Figure 2:
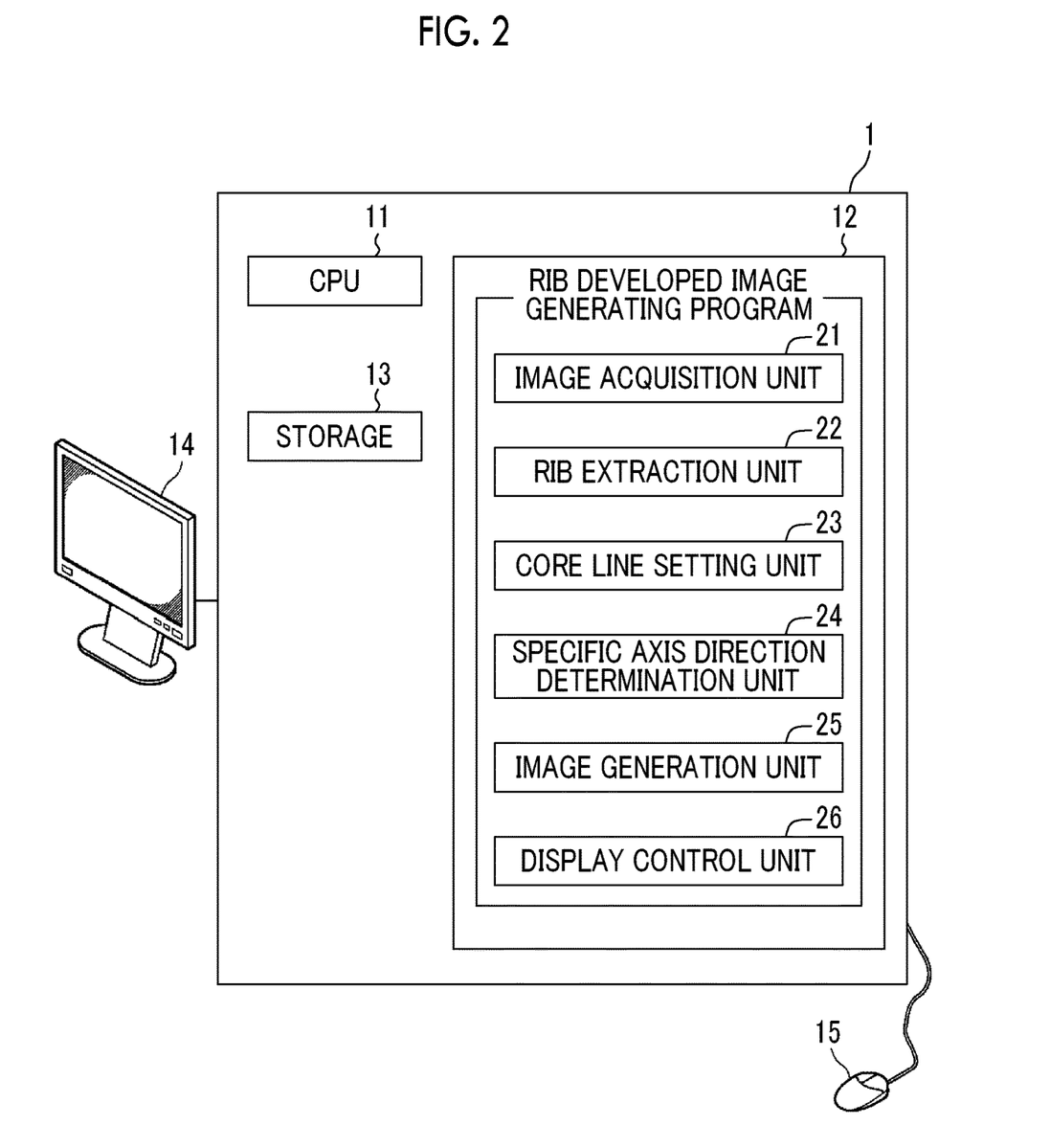
FIG. 2 is a schematic block diagram showing the configuration of the rib developed image generation apparatus according to the present embodiment.

FIG. 2 is a diagram showing the schematic configuration of a rib developed image generation apparatus realized by installing a rib developed image generation program on a computer. As shown in FIG. 2, the rib developed image generation apparatus 1 comprises a central processing unit (CPU) 11, a memory 12, and a storage 13 as the configuration of a standard workstation. A display 14, such as a liquid crystal monitor, and an input unit 15, such as a keyboard and a mouse, are connected to the rib developed image generation apparatus 1. The display 14 corresponds to a display unit.

Three-dimensional images of the subject acquired from the image storage server 3 through the network 4 and various kinds of information including information necessary for processing are stored in the storage 13.

A rib developed image generation program is stored in the memory 12. As processing to be executed by the CPU 11, the rib developed image generation program defines: image acquisition processing for acquiring a three-dimensional image G0 acquired by the three-dimensional image capturing apparatus 2; rib extraction processing for extracting at least one rib from the three-dimensional image G0; core line setting processing for setting the core line of at least one rib; specific axis direction determination processing for determining a specific axis direction in a cross section crossing the core line of the at least one rib; image generation processing for moving a position of the core line in the specific axis direction according to an instruction to move the core line in the specific axis direction and generating a developed image of the at least one rib based on a cross section along the core line at the moved position; and display control processing for displaying the developed image on the display 14.

The CPU 11 executes these processes according to the program, so that the computer functions as an image acquisition unit 21, a rib extraction unit 22, a core line setting unit 23, a specific axis direction determination unit 24, an image generation unit 25, and a display control unit 26. In the present embodiment, the CPU 11 executes the function of each unit according to the rib image generation program. However, as a general-purpose processor that executes software to function as various processing units, a programmable logic device (PLD) that is a processor whose circuit configuration can be changed after manufacturing, such as a field programmable gate array (FPGA), can be used in addition to the CPU 11. In addition, the processing of each unit may also be executed by a dedicated electric circuit that is a processor having a circuit configuration designed exclusively to execute specific processing, such as an application specific integrated circuit (ASIC).

One processing unit may be configured by one of various processors, or may be a combination of two or more processors of the same type or different types (for example, a combination of a plurality of FPGAs or a combination of a CPU and an FPGA). In addition, a plurality of processing units may be configured by one processor. As an example of configuring a plurality of processing units using one processor, first, as represented by a computer, such as a client or a server, there is a form in which one processor is configured by a combination of one or more CPUs and software and this processor functions as a plurality of processing units. Second, as represented by a system on chip (SoC) or the like, there is a form of using a processor that realizes the function of the entire system including a plurality of processing units with one integrated circuit (IC) chip. Thus, various processing units are configured by using one or more of the above-described various processors as a hardware structure.

More specifically, the hardware structure of these various processors is an electrical circuit (circuitry) in the form of a combination of circuit elements, such as semiconductor elements.

The image acquisition unit 21 acquires the three-dimensional image G0 of the chest including the ribs as a diagnosis target part from the image storage server 3. In a case where the three-dimensional image G0 is already stored in the storage 13, the image acquisition unit 21 may acquire the three-dimensional image G0 from the storage 13.

The rib extraction unit 22 extracts at least one rib from the three-dimensional image G0. In the present embodiment, the rib extraction unit 22 extracts a plurality of ribs from the three-dimensional image G0. In the three-dimensional image G0 that is a CT image, the bone tissue has a higher CT value than the soft tissue. For this reason, the rib extraction unit 22 extracts a bone region from the three-dimensional image G0 by threshold value processing. Alternatively, a bone region may be extracted from the three-dimensional image G0 using a discriminator learned to discriminate a bone region.

Then, the rib extraction unit 22 specifies a vertebra in the extracted bone region. Specification of a vertebra is performed by template matching using a template showing the shape of the vertebra. Alternatively, a vertebra may be specified using a discriminator learned to discriminate the vertebra.

Figure 3:
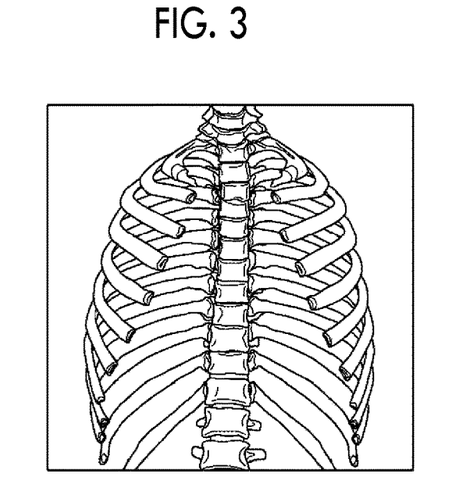
FIG. 3 is a diagram showing extracted ribs.

Here, the rib is an arcuate bone extending from the thoracic vertebrae, which are a part of the vertebral body forming the vertebrae, to the left and right sides. The rib extraction unit 22 detects a part of a bone region extending in the horizontal direction with each of the first vertebral body to the twelfth vertebral body, among the vertebral bodies included in the specified vertebrae, as a starting point and extends the bone region with the detected part as a starting point, thereby extracting right first to twelfth ribs and left first to twelfth ribs. Ribs are connected to the sternum through the costal cartilage, but the costal cartilage is not extracted as a bone region by threshold value processing for extracting the bone region. For this reason, as shown in FIG. 3, the rib extraction unit 22 extracts the right first to twelfth ribs and the left first to twelfth ribs excluding the costal cartilage. Alternatively, ribs may be extracted from the bone region using a discriminator learned to discriminate the ribs.

Figure 4:
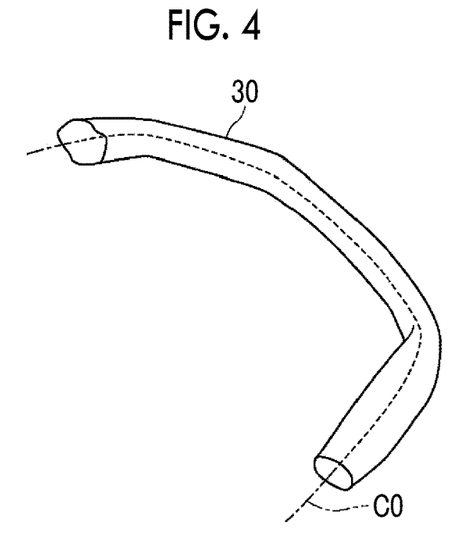
FIG. 4 is a diagram showing a core line set in one rib.

The core line setting unit 23 sets the core line of the rib extracted by the rib extraction unit 22. The core line is the center line of the ribs connecting the centers (centers of gravity) of the cross sections of the ribs. In the present embodiment, the core line setting unit 23 calculates eigenvalues of 3×3 Hessian matrix for each local region in each rib, and sets a core line based on the calculated eigenvalues. Here, in a region including a linear structure such as a rib, one of the three eigenvalues of the Hessian matrix is a value close to 0, and the other two are relatively large values. The eigenvector corresponding to the eigenvalue close to 0 indicates the main axis direction of the linear structure. The core line setting unit 23 determines the likeliness of a linear structure based on the eigenvalues of the Hessian matrix for each local region of each rib, and detects the center point as a candidate point of the core line for the local region for which the linear structure is identified. Then, the core line setting unit 23 sets the core line of each rib by connecting the detected candidate points. FIG. 4 is a diagram showing a core line C0 set in one rib. In FIG. 4, the core line C0 passing through the inside of a rib 30 is indicated by a broken line, and the core line C0 outside the rib 30 is indicated by a one-dot chain line.

The method of setting the core line C0 is not limited thereto, and any other methods can be used. For example, the core line C0 may be set using a thinning method. In addition, the core line C0 may be set while extracting a rib region from the three-dimensional image G0 using a method of extracting blood vessels disclosed in JP2004-313736A. Alternatively, the three-dimensional image G0 displayed by the volume rendering method or the like may be displayed on the display 14, the center point of the cross section of each rib may be manually input on the displayed image using an input device, such as a mouse, and a plurality of input points may be set by spline interpolation to set the core line C0.

Figure 5:
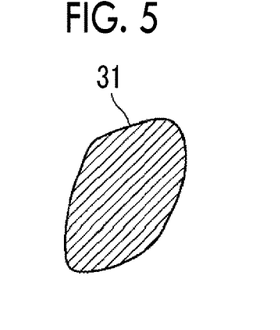
FIG. 5 is a diagram showing a cross section perpendicular to the core line of a rib.
Figure 6:
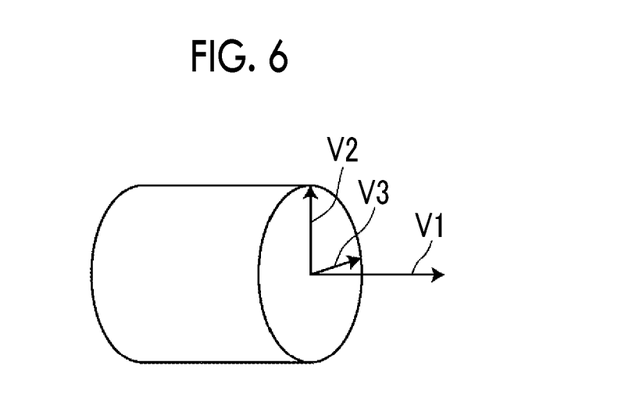
FIG. 6 is a diagram showing the result of main component analysis.

The specific axis direction determination unit 24 determines a specific axis direction in a cross section crossing the core line C0 of the rib. In the present embodiment, the specific axis direction determination unit 24 determines the short axis direction of a cross section perpendicular to the core line C0 of the rib as the specific axis direction. FIG. 5 is a diagram showing a cross section perpendicular to the core line C0 of the rib. As shown in FIG. 5, a cross section 31 perpendicular to the core line C0 of the rib has a shape approximate to an ellipse. For each rib in the three-dimensional image G0, the specific axis direction determination unit 24 calculates a differential value of each pixel in a predetermined range (for example, a cube having a side of 20 mm considering the thickness of the rib) from the position of the core line C0, and performs main component analysis of the differential value. As shown in FIG. 5, the cross section 31 perpendicular to the core line C0 of the rib can be approximated by an ellipse. Therefore, as shown in FIG. 6, the specific axis direction determination unit 24 calculates a vector V1 in the direction of the core line C0, a vector V2 in the long axis direction of the cross section, and a vector V3 in the short axis direction of the cross section by main component analysis. Then, the specific axis direction determination unit 24 determines the direction of the vector V3 calculated by the main component analysis, that is, the short axis direction of the cross section, as the specific axis direction. Alternatively, the specific axis direction determination unit 24 may determine a specific axis direction in a plurality of cross sections of one rib at predetermined intervals on the core line C0 of each rib. In this case, one direction representing the specific axis direction determined in each cross section may be determined as the specific axis direction of the rib. As one representative direction, for example, it is possible to use a direction obtained by averaging a plurality of specific axis directions or a direction as a median value of a plurality of specific axis directions.

In the present embodiment, the specific axis direction is determined in each of a plurality of ribs. However, one direction representing the specific axis direction determined in each of the plurality of ribs may be determined as one specific axis direction for all of the plurality of ribs. As one representative direction, for example, it is possible to use a direction obtained by averaging the specific axis directions of a plurality of ribs or a direction as a median value of the specific axis directions of the plurality of ribs.

In the cross sections of all the ribs, the short axis direction substantially faces the front-back direction of the human body. For this reason, in a case where a specific axis direction is determined for each of a plurality of ribs, the specific axis directions of the plurality of ribs are mostly the same direction.

Figure 7:
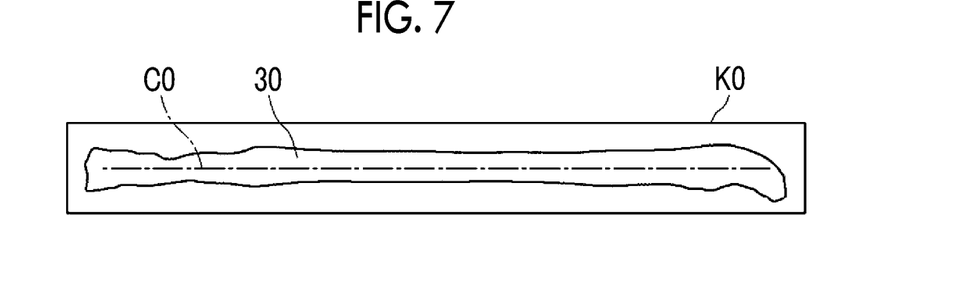
FIG. 7 is a diagram showing a developed image of one rib.

The image generation unit 25 moves the position of the core line C0 in the specific axis direction according to an instruction to move the core line C0 in the specific axis direction, and generates a developed image of the rib based on the cross section along the core line C0 at the moved position. The instruction to move the core line C0 is given from the operator through the input unit 15. In the present embodiment, the image generation unit 25 sets a cross section, which passes through the core line C0 and is perpendicular to the specific axis direction, for each rib. Then, the image generation unit 25 cuts each rib in the set cross section to generate a developed image. The developed image generated in the present embodiment is a straightened CPR image, but a stretched CPR image or a projected CPR image may be used. FIG. 7 is a diagram showing a developed image of one rib. As shown in FIG. 7, a developed image K0 is an image in which the rib 30 is developed along the core line C0.

Figure 8:
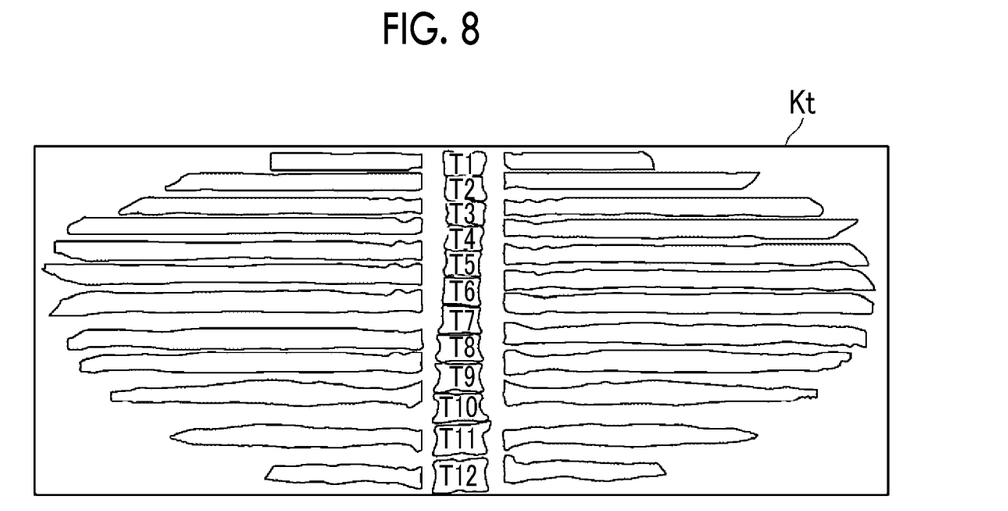
FIG. 8 is a diagram showing a combined image obtained by combining developed images of a plurality of ribs.

The display control unit 26 displays the developed image K0 generated by the image generation unit 25 on the display 14. In the present embodiment, a combined image Kt obtained by combining the developed images K0 of a plurality of ribs, is displayed on the display 14. In this case, the combined image Kt in which the developed images K0 of the plurality of ribs are associated with the vertebrae is displayed on the display 14. FIG. 8 is a diagram showing a combined image displayed on the display 14. As shown in FIG. 8, in the combined image Kt, developed images of a plurality of ribs are displayed so as to be associated with vertebrae T1 to T12.

In a case where the core line C0 is moved, the image generation unit 25 generates a developed image of each rib at the moved position of the core line C0. Assuming that the position of the core line C0 expressed by the three-dimensional coordinates in the cross section of each rib is Pi and the vector in the specific axis direction in each cross section of the rib is V3$i$, the position of the core line C0 after movement in each cross section can be expressed by the following Equation (1). In Equation (1), d is a movement amount. The image generation unit 25 generates a developed image of each rib based on the cross section along the core line C0 at each moved position.

$$\text{Position of core line} = Pi + d \times V3i \qquad (1)$$

In a case where the core line C0 is moved in this manner, the cross section to generate a developed image in the specific axis direction is moved for all the ribs. In the present embodiment, the cross section perpendicular to the core line C0 of the rib has a long axis in the vertical direction of the human body (that is, the body axis direction) and has a short axis in the front-back direction of the human body. Therefore, moving the core line C0 in the specific axis direction is substantially equivalent to moving the cross section of the rib in the front-back direction of the human body.

Figure 9:
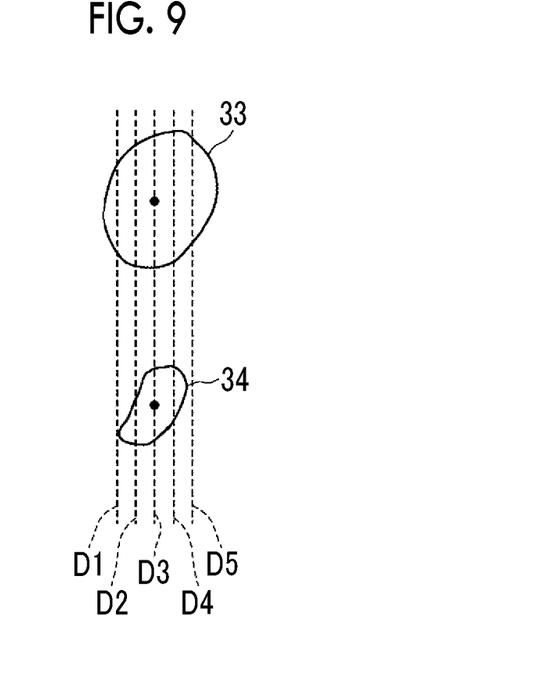
FIG. 9 is a diagram showing a cross section in a case where the core line is moved at equal intervals in a specific axis direction.

In the above Equation (1), d is a movement amount. Therefore, in a case where the developed image K0 is generated by applying Equation (1) for each rib, the core line C0 is moved at equal intervals in all the ribs. For this reason, in the case of a thin rib, the rib is no longer included in the developed image K0 depending on the position of the core line C0. That is, as shown in FIG. 9, for a thick rib 33 and a thin rib 34, it is considered to generate a developed image in five cross sections D1 to D5 by moving the core line C0 in the specific axis direction. In this case, in the cross sections D2 to D4, ribs are included in the developed image in both the thick rib 33 and the thin rib 34. However, in the cross sections D1 and D5, ribs are included in the developed image of the thick rib 33, but ribs are no longer included in the developed image of the thin rib 34.

Figure 10:
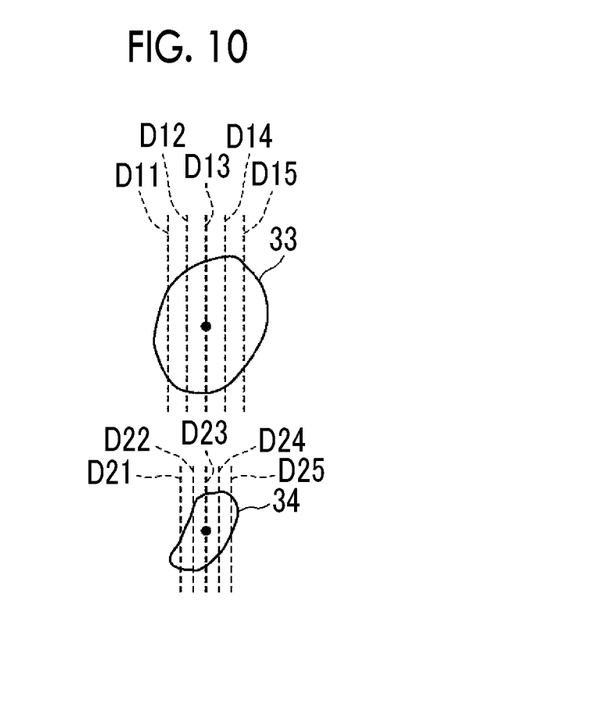
FIG. 10 is a diagram showing a cross section in a case where the core line is moved at a rate corresponding to the length in the specific axis direction.

For this reason, the core line C0 may be moved by the following Equation (2). In Equation (2), D is a distance from the core line C0 of each rib to the surface in the specific axis direction (that is, the short axis direction), and r is a ratio ($-0.5 \leq r \leq 0.5$). In this case, according to an instruction to move the core line C0, the value of r is changed in each rib to generate the developed image K0. As a result, as shown in FIG. 10, even in a case where a developed image is generated in five cross sections D11 to D15 of the thick rib 33, it is possible to generate a developed image in five cross sections D21 to D25 of the thin rib 34. Therefore, irrespective of the thickness of the rib, ribs can be included in the developed image K0 of a plurality of ribs at the position of any core line C0.

$$\text{Position of core line} = P_i + D \times r \times V3_i \qquad (2)$$

In a case where the specific axis direction determination unit 24 determines one specific axis direction for a plurality of ribs, the core line C0 may be moved in the specific axis direction. In addition, in a case where the specific axis direction determination unit 24 determines a feature point axis direction for each of a plurality of ribs, the core line C0 may be moved in the specific axis direction corresponding to each rib.

Figure 11:
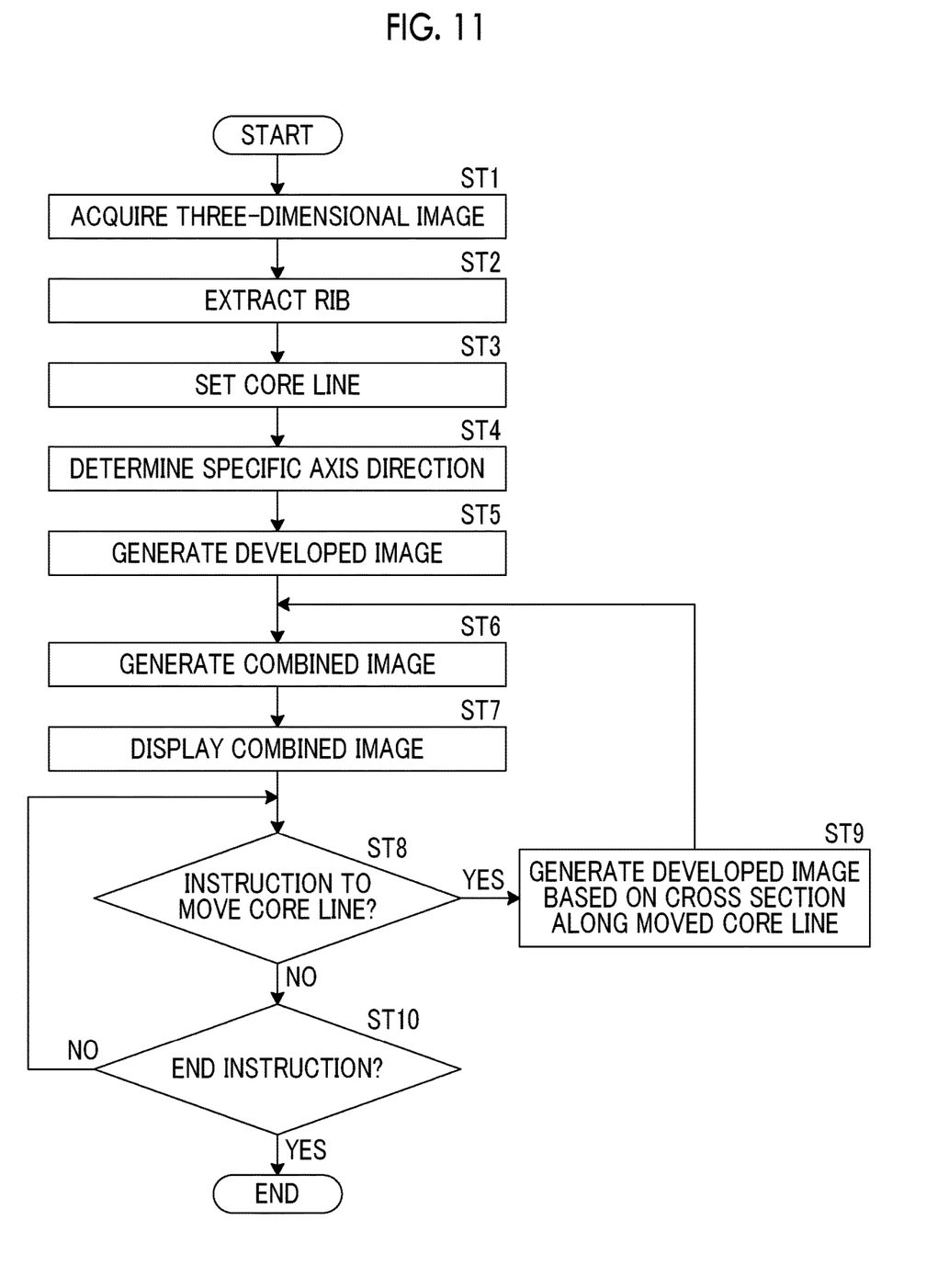
FIG. 11 is a flowchart showing a process performed in the present embodiment.

Next, a process performed in the present embodiment will be described. FIG. 11 is a flowchart showing the process performed in the present embodiment. First, the image acquisition unit 21 acquires the three-dimensional image GO (step ST1), and the rib extraction unit 22 extracts a rib from the three-dimensional image GO (step ST2). Then, the core line setting unit 23 sets the core line C0 of the rib (step ST3), and the specific axis direction determination unit 24 determines a specific axis direction in a cross section crossing the core line C0 of the rib (step ST4). Then, the image generation unit 25 generates the developed image K0 of the rib based on the cross section along the core line C0 in each rib (step ST5). Then, the display control unit 26 combines a plurality of developed images K0 to generate the combined image Kt (step ST6), and displays the combined image Kt on the display 14 (step ST7).

On the other hand, in a case where there is an instruction to move the core line C0 in the specific axis direction through the input unit 15 (YES in step ST8), the image generation unit 25 moves the position of the core line in the specific axis direction in response to the instruction to move the core line in the specific axis direction and generates a developed image of the rib based on the cross section along the core line at the moved position (step ST9), and the process returns to step ST6. In a case where the result in step ST8 is negative, it is determined whether or not an end instruction has been given (step ST10). In a case where the result in step ST10 is negative, the process returns to step ST7. In a case where the result in step ST10 is positive, the process is ended.

As described above, in the present embodiment, the position of the core line C0 is moved in the specific axis direction according to an instruction to move the core line C0, and the developed image K0 of the rib is generated based on the cross section along the core line C0 at the moved position. For this reason, even in a case where the core line C0 is moved, the direction of the cross section defined by the generated developed image K0 is not changed. Therefore, even in a case where the cross section where the developed image K0 is generated in the rib is changed, the direction in the human body is not changed in the displayed developed image K0. Specifically, in the present embodiment, the cross section of the rib is moved mostly in the front-back direction of the human body. Therefore, in a case where the developed image K0 of whichever cross section is displayed, it is possible to recognize which direction in the human body the cross section of the developed image K0 faces.

In the embodiment described above, the combined image Kt obtained by combining the developed images K0 of a plurality of ribs is displayed on the display 14. However, the developed image K0 of one rib may be displayed on the display 14.

Figure 12:
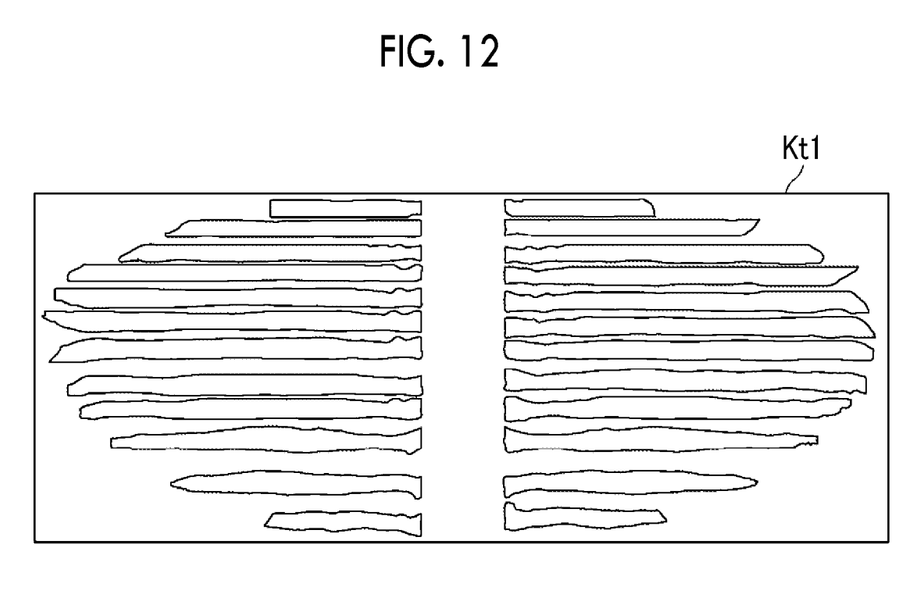
FIG. 12 is a diagram showing another example of a combined image obtained by combining developed images of a plurality of ribs.

In the embodiment described above, in the combined image Kt, developed images of a plurality of ribs are displayed so as to be associated with the vertebrae T1 to T12. However, as shown in FIG. 12, a combined image Kt1 obtained by combining only the developed images of a plurality of ribs may be displayed on the display 14 without associating the developed images with the vertebrae.

Hereinafter, the effect of the present embodiment will be described.

By displaying a combined image obtained by combining the developed images of a plurality of ribs, it is possible to recognize the state of a plurality of ribs at once.

By displaying a combined image such that a plurality of ribs are associated with vertebrae, it is possible to recognize the state of the plurality of ribs at once while checking the positional relationship between the plurality of ribs and the vertebrae.

Since a rib has a different thickness depending on its position, the length in the specific axis direction is different. Therefore, by moving the core line at a rate corresponding to the length in the specific axis direction for a plurality of ribs, it is possible to always display developed images of the plurality of ribs even in a case where a cross section to display the developed images of the plurality of ribs is changed.

What is claimed is:

1. A rib developed image generation apparatus, comprising:
   a processor configured to:
   extract at least one rib from a three-dimensional image including ribs;
   set a core line of the at least one rib;
   determine a specific axis direction in a cross section crossing the core line of the at least one rib; and
   move a position of the core line in the specific axis direction according to an instruction to move the core line in the specific axis direction and generate a developed image of the at least one rib based on a cross section along the core line at the moved position.

2. The rib developed image generation apparatus according to claim 1,
   wherein the processor displays the developed image on a display.

3. The rib developed image generation apparatus according to claim 2,
wherein the processor displays a combined image, which is obtained by combining the developed images of a plurality of ribs, on the display.

4. The rib developed image generation apparatus according to claim 3,
wherein the processor displays the combined image on the display such that the plurality of ribs are associated with vertebrae.

5. The rib developed image generation apparatus according to claim 3,
wherein the processor moves the core line at equal intervals in the specific axis direction for the plurality of ribs.

6. The rib developed image generation apparatus according to claim 3,
wherein the processor the core line at a rate corresponding to a length in the specific axis direction for the plurality of ribs.

7. A rib developed image generation method, comprising:
extracting at least one rib from a three-dimensional image including ribs;
setting a core line of the at least one rib;
determining a specific axis direction in a cross section crossing the core line of the at least one rib; and
moving a position of the core line in the specific axis direction according to an instruction to move the core line in the specific axis direction and generating a developed image of the at least one rib based on a cross section along the core line at the moved position.

8. A non-transitory computer-readable storage medium that stores a rib developed image generation program causing a computer to execute:
extracting at least one rib from a three-dimensional image including ribs;
setting a core line of the at least one rib;
determining a specific axis direction in a cross section crossing the core line of the at least one rib; and
moving a position of the core line in the specific axis direction according to an instruction to move the core line in the specific axis direction and generating a developed image of the at least one rib based on a cross section along the core line at the moved position.

* * * * *